United States Patent [19]

Lindley et al.

[11] Patent Number: 5,068,448

[45] Date of Patent: Nov. 26, 1991

[54] PROCESS FOR THE PRODUCTION OF 4'-ISOBUTYLACETOPHENONE

[75] Inventors: Daniel D. Lindley, Portland, Tex.; Thomas A. Curtis, Tega Cay, S.C.; Timothy R. Ryan, Corpus Christi, Tex.; Edward M. de la Garza, Corpus Christi, Tex.; Charles B. Hilton, Corpus Christi, Tex.; Thomas M. Kenesson, Corpus Christi, Tex.

[73] Assignee: Hoechst Celanese Corporation, Somerville, N.J.

[21] Appl. No.: 593,143

[22] Filed: Oct. 5, 1990

Related U.S. Application Data

[63] Continuation-in-part of Ser. No. 445,055, Dec. 4, 1989, Pat. No. 4,990,681.

[51] Int. Cl.$^5$ .............................................. C07C 45/45
[52] U.S. Cl. ...................................... 568/319; 568/324
[58] Field of Search ................................. 568/319, 323

[56] References Cited

U.S. PATENT DOCUMENTS

| | | | |
|---|---|---|---|
| 3,385,886 | 5/1968 | Nicholson et al. | 568/319 |
| 3,403,183 | 9/1968 | Dobratz et al. | 568/319 |
| 4,894,482 | 1/1990 | Lindley et al. | 568/319 |
| 4,967,011 | 10/1990 | Tokura et al. | 568/324 |

FOREIGN PATENT DOCUMENTS 85188343  9/1985  Japan .................................. 568/319

OTHER PUBLICATIONS

Baddeley et al., *Journal of the Chemical Society*, (1956): 4943–4945.

*Primary Examiner*—James H. Reamer
*Attorney, Agent, or Firm*—Shirley L. Church; Marvin Turken

[57] ABSTRACT

A continuous process is provided for the production of 4'-isobutylacetophenone (4-IBAP) comprising feeding liquid hydrogen fluoride (HF) and an acetylating agent into an extractor-reactor to form a first, HF-rich phase containing the acetylating agent, feeding isobutylbenzene (IBB) to the extractor-reactor to form a second, IBB-rich phase which is contacted with said first, HF-rich phase in a manner such that the acetylating agent reacts with IBB to form 4-IBAP which is extracted into the first, HF-rich phase, and a light IBB-rich second phase containing the bulk of unreacted IBB, externally recycling said second, IBB-rich phase to the IBB feed point in combination with fresh IBB to make up for IBB consumed in the reaction and that and dissolved in the HF-rich phase, and withdrawing HF-rich phase containing 4-IBAP from the extractor-reactor.

24 Claims, 2 Drawing Sheets

PROCESS FOR THE PRODUCTION OF 4'-ISOBUTYLACETOPHENONE

CROSS-REFERENCE TO RELATED APPLICATIONS

This application is a continuation-in-part of application Ser. No. 07/445,055, filed Dec. 4, 1989, now U.S. Pat. No. 4,990,681.

BACKGROUND OF THE INVENTION

1. Field of the Invention

This invention relates to an improved process for the production of 4'-isobutylacetophenone (4-IBAP). Various processes are known in which 4-IBAP is used as an intermediate in the production of ibuprofen, a widely used nonsteroidal anti-inflammatory drug which has been converted from ethical, i.e., prescription, to over-the-counter status.

2. Description of Related Art

The following information is disclosed in accordance with the terms of 37 CFR 1.56, 1.97 and 1.98.

U.S. Pat. No. 3,385,886, shows the production of phenylalkane derivatives such as ibuprofen in which the first step of the process is the reaction of a phenylalkane with acetyl chloride in the presence of aluminum chloride to produce an alkylphenylacetophenone.

Japanese Patent Publication (Early Disclosure) No. 60 [1985]-188,343, discloses the preparation of p-isobutylacetophenone by the acetylation of isobutylbenzene using as an acetylating agent acetyl fluoride prepared by reacting acetic anhydride with hydrogen fluoride, and as a catalyst, a combination of hydrogen fluoride and boron trifluoride.

Baddely et al., Journal of the Chemical Society, 4943-4945 [1956], discloses on page 4945 the preparation of 4'-isobutylacetophenone by the Friedel-Crafts acetylation of isobutylbenzene with acetyl chloride using aluminum chloride as a catalyst.

Pending application Ser. No. 158,141 filed Mar. 4, 1988 by Elango et al., shows the production of 4'-isobutylacetophenone (4-IBAP) by the Friedel-Crafts acetylation of isobutylbenzene (IBB) with an acetylating agent which may be acetyl fluoride (AcF) or acetic anhydride (Ac2O), using a catalyst which may be hydrogen fluoride. The 4'-isobutylacetophenone is disclosed as an intermediate in a process for the production of ibuprofen.

Parent application Ser. No. 07/445,055 filed Dec. 4, 1989, discloses the operation of an extractor reactor to produce 4IBAP and the removal of HF from the product of the latter operation by reacting the HF with acetic anhydride in an HF removal column, both contemplated under the invention of this application. The entire disclosure of this application is incorporated by reference.

SUMMARY OF THE INVENTION

A disadvantage of the production of IBAP by reacting isobutylbenzene (IBB) with an acetylating agent in hydrogen fluoride (HF) as a catalyst/solvent is that IBB is not appreciably soluble in HF. This restricts the contact between the IBB and the acetylating agent and has the effect of reducing the rate of reaction.

In accordance with this invention, 4-IBAP is produced in a continuous process wherein IBB is reacted with an acetylating agent in the presence of liquid HF as a catalyst/solvent, in an extraction-reaction zone, i.e., a unitary extractor-reactor. The IBB which is lighter than and substantially insoluble in HF, forms an IBB-rich phase, e.g., as droplets, which percolates upwardly through an HF-rich phase containing the acetylating agent. The formed 4-IBAP is selectively soluble in and is extracted into the HF-rich phase, while the bulk of unreacted IBB is withdrawn and externally recycled to the vessel with a fresh supply of IBB. The recycled IBB may be further purified prior to feeding it back to the extractor-reactor. A product stream is withdrawn from the vessel and comprises 4-IBAP, HF, a small amount of IBB, and in many cases, varying amounts of acetic acid and acetyl fluoride, the specific amounts of these components depending among other factors on the nature of the acetylating agent initially added. As used in this specification, the terms "feed point" or "point of withdrawal" may mean one or more points in the vessel at which the designated stream is fed or withdrawn.

Because IBB is slightly soluble in the HF-rich phase, that portion of such phase below the feed point of fresh and recycled IBB will often contain a small amount of IBB. Since this amount could be economically important, it is another aspect of this invention to provide additional residence time between the feed point of IBB and point of withdrawal of the product stream, i.e., a "finishing zone," such that a significant proportion of the IBB dissolved in the HF-rich phase has an opportunity to react with acetylating agent remaining in such phase to produce an additional amount of 4-IBAP. Such finishing zone may be, for example, the bottom portion, below the IBB feed point, of the extractor-reactor vessel which contains only an HF-rich phase with dissolved IBB in the absence of any substantial amount of IBB-rich phase. Alternatively, or in addition to the foregoing expedient, the product stream may be transferred to and held in a separate vessel as the finishing zone, i.e., a "finishing reactor," for a period and under conditions to obtain further acetylation of dissolved IBB in a homogeneous system.

In accordance with another aspect of the invention, the operation of the extractor-reactor described previously is combined in an integrated process with the operation of an HF removal column utilizing acetic anhydride (Ac2O) to react with the HF in the 4-IBAP/HF and acetic acid/HF complexes present in the product of the extractor-reactor, forming acetyl fluoride (AcF) which together with free liberated HF is withdrawn as an overhead stream, with at least part of such stream being recycled to the extractor-reactor. The bottoms stream from the HF-removal column comprises 4-IBAP and acetic acid (HOAc) at least some of which acid is produced in the foregoing reaction.

In accordance with still another aspect of the invention, the bottom stream from the HF removal column is fed to a light ends column where the bulk of the acetic acid is separated from the 4-IBAP, with at least part of the acetic acid being recycled to the extractor-reactor.

DESCRIPTION OF PREFERRED EMBODIMENTS

Figure 1:
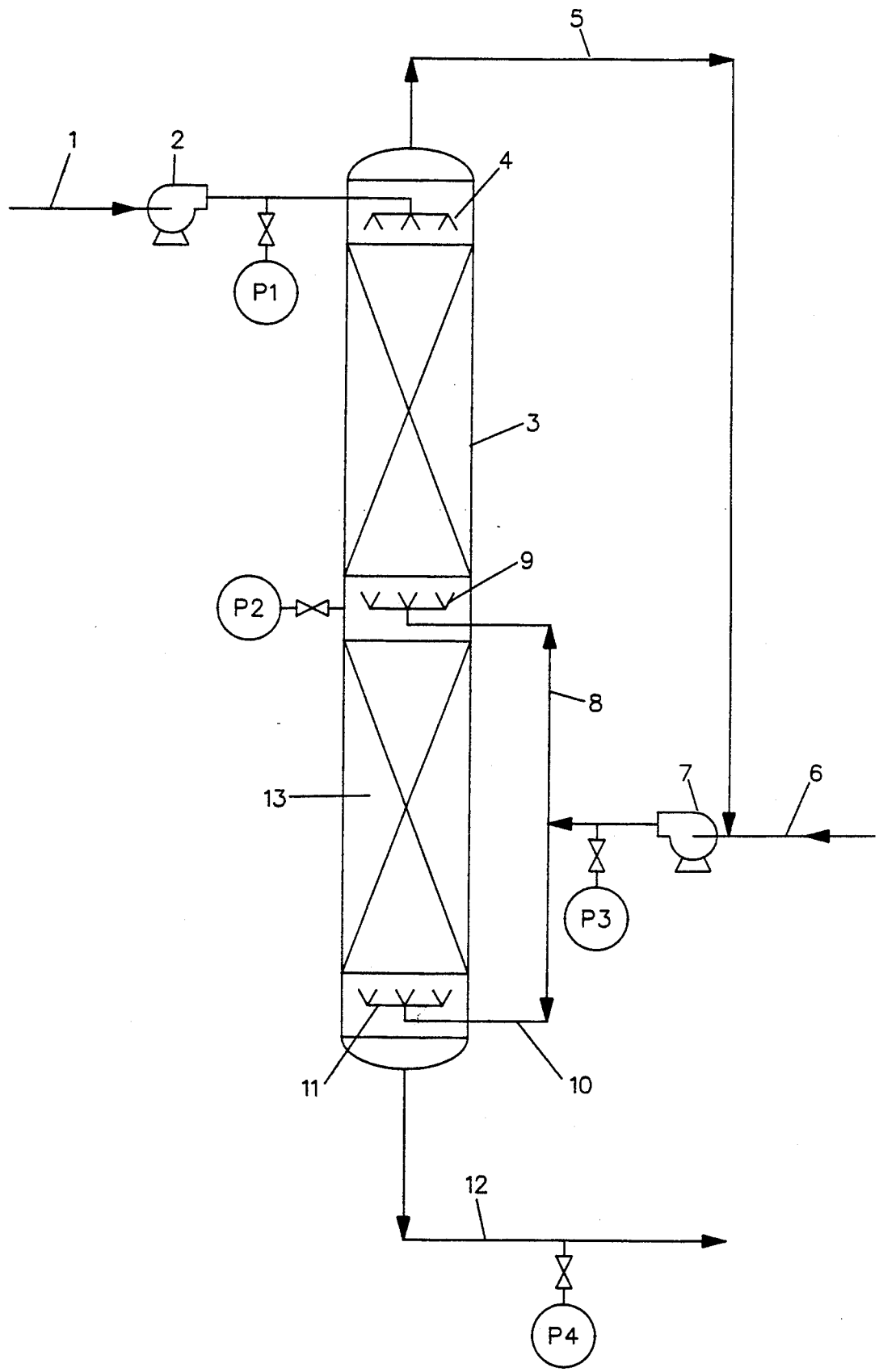
FIG. 1 is a schematic diagram of a process for producing 4-IBAP utilizing an extractor-reactor and optional finishing zone contemplated under this invention.

The reaction carried out by the process of this invention is shown in the following equation:

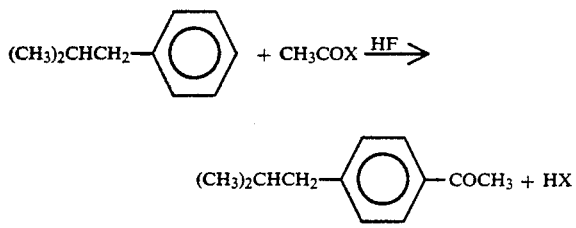

where "X" is the residue minus the acetyl group of an effective acetylating agent. Acetylating agents which may be used are, for example, acetyl fluoride (X=F), acetic anhydride (X=—OCOCH$_3$) and acetic acid (X=—OH). Mixtures of acetylating agents may also be used and form in situ if certain acetylating agents such as acetic anhydride, are used. The acetic anhydride reacts with IBB to form 4-IBAP and acetic acid which is also an acetylating agent. Moreover, acetic anhydride also reacts with HF to form acetyl fluoride, another acetylating agent and acetic acid. If free acetic acid is used as all or part of the acetylating agent, some of its anhydride may be added to further react with the water of reaction. Alternatively, acetyl fluoride if present will also react with water of reaction to form HF and acetic acid. The product of the reaction thus comprises 4-IBAP and HF and/or free acetic acid, with HF being present in appreciable amount in either case because of the large excess used as solvent/extractant/catalyst, e.g., about 7 to 80 moles per mole of IBB/4-IBAP. The recycle ratio, i.e., the ratio of the weight of IBB-rich phase being recycled from at or near the top to the IBB feed point, preferably below the feed point of HF and acetylating agent in the reactor, to the total weight of material entering or leaving the reactor at steady state, may be in the range, for example, of about 2 to 0.03, preferably about 0.5 to 0.1. The use of packing in the extractor-reactor is beneficial in that it increases the efficiency of HF-rich phase/IBB-rich phase contact and helps to provide "plug flow" of the IBB-rich phase, which is preferably the discontinuous phase, through the HF-rich phase, which is preferably the continuous phase. The reaction may be carried out a temperature, for example of about 45° to 80° C., at a pressure which prevents boiling, for example, a pressure of about 35 to 150 psig over a residence time of, for example, about 0.3 to 4 hours.

As stated, the product of the extractor-reactor may pass through a finishing zone of the extractor-reactor or may be sent to a separate finishing reactor to maximize the homogeneous phase conversion of IBB to 4-IBAP. Such finishing zone or reactor may be operated at a temperature and pressure similar to those of the extractor-reactor and, for a residence time, for example of about 0.1 to 4 hours, preferably about 0.5 to 2 hours. The finishing zone or reactor can be used in a plug flow arrangement (by packing the reactor) or in a laminar flow arrangement.

The product stream withdrawn from the extractor-reactor or the finishing reactor contains free, i.e., substantially uncomplexed HF, and HF which is complexed with 4-IBAP and, if acetyl fluoride, acetic anhydride or acetic acid is used as all or part of the acetylating agent, also contains HF, water and/or acetic acid respectively formed as a by-product of the acetylation reaction. Some of the acetic acid present also tends to form a complex with HF. Additionally, the product stream may also contain unreacted isobutylbenzene (IBB), acetyl fluoride (AcF), acetic acid (HOAc) and acetic anhydride (Ac$_2$O), depending on the extent of the reaction or initial stoichiometric ratios employed.

To separate both the uncomplexed and complexed HF from the 4-IBAP and acetic acid in the product stream from the extractor-reactor, such stream may be sent to an HF-removal column, the operation of which is disclosed in parent application Ser. No. 07/45.055, the entire disclosure of which is incorporated by reference. In such operation, acetic anhydride (Ac$_2$O) is added to the column below the feed point of the entering stream and reacts with the complexed HF to form acetyl fluoride (AcF) and acetic acid (HOAc) as shown in the following equation:

$$Ac_2O + HF \rightarrow AcF + HOAc$$

The acetyl fluoride is relatively volatile and is withdrawn from the top of the column with the initially uncomplexed HF, which is separated and rises from the entering stream at or near its feed point. Some IBB, if present, can also be collected overhead for recycle back to the reactor. A less volatile stream comprising 4-IBAP and acetic acid is withdrawn from the bottom of the column. The reaction and stripping operations occurring in the HF-removal column may be carried out at a temperature, for example of about 30° to 155° C. and a pressure, for example, of about 0 to 25 psig.

To further purify the desired 4-IBAP product and partially recover some of the acetyl values of the system, the bottom stream from the HF-removal column may be sent to a light ends column where 4-IBAP and heavier components leaving the bottom of the column ar separated from acetic acid which leaves the top of the column and part of which may be recycled to the extractor-reactor where it may serve as part of the acetylating agent. The light ends column may be operated using a bottoms temperature, for example, of about 160° to 200° C. and a pressure of about 30 to 110 mm Hg. If desired, the bottom stream from the light ends column may be sent to a heavy ends column where the 4-IBAP is further purified by removal of most of the heavier impurities with which it is mixed in such bottom stream.

Referring now to FIG. 1, a stream comprising a mixture of liquid HF and acetylating agent entering the system through line 1 is continuously sent by pump 2 into extractor-reactor 3 where it is ejected as several streams from multi-opening liquid distributor 4 below a light IBB-rich phase collected at the top of the extractor-reactor 3. The mixture comprising HF and acetylating agent forms a dense, preferably continuous HF-rich phase traveling downwardly through extractor-reactor 3. IBB-rich light phase is withdrawn from the top of extractor-reactor 3 and flows through line 5 as an IBB recycle stream. Fresh IBB flows from a makeup source through line 6 where it is combined with the IBB recycle stream from line 5. By means of a valve adjustment (not shown), the combined IBB feed is propelled by pump 7 through line 8 and thence into the middle of extractor-reactor 3 through multi-opening liquid distributor 9. In the alternative, if a separate finishing reactor (not shown) is employed, combined IBB feed may enter through line 10 and into the bottom of extractor-reactor 3 through multi-opening liquid distributor 11. In either case, in the preferred embodiment of the invention shown in FIG. 1, the IBB feed stream forms a discontinuous light IBB-rich phase which percolates upwardly through the continuous, dense HF-rich phase. As it does so, IBB reacts with acetylating agent to form 4-IBAP, HF, $H_2O$ and/or acetic acid by-product (as explained previously) which are absorbed into the continuous dense HF-rich phase. Such dense phase containing 4-IBAP, HF, and in most cases, some acetic acid and AcF is withdrawn as reactor product through line 12. Some of the discontinuous light IBB-rich phase containing unreacted IBB collects at the top of extractor-reactor 3 and is recycled through line 5 as previously described.

In addition to reacting with acetylating agent in the continuous, dense HF-rich phase to form 4-IBAP, some of the IBB in the discontinuous light IBB-rich phase remains unreacted and dissolves in the dense HF-rich phase which may therefore contain on the order of about 1 to 10 wt.% of dissolved IBB. If the IBB feed stream enters extractor-reactor 3 at its center through line 8 and liquid distributor 9, an HF-rich liquid containing acetylating agent and some dissolved IBB moves downward from liquid distributor 9 to the bottom of extractor-reactor 3 where the reactor product is withdrawn through line 12. This provides residence time for a portion of the dissolved IBB to further react with acetylating agent in a homogeneous system to form additional 4-IBAP. In view of this operation, the lower portion of extractor-reactor 3 indicated in FIG. 1 by numeral 13, may be termed a "finishing zone." As stated, the same reaction may be carried out in a "finishing reactor" which is a vessel entirely separate from the extractor-reactor.

The designations P1, P2, P3 and P4 in FIG. 1 indicate primary sample points from which samples may be periodically withdrawn and analyzed.

Figure 2:
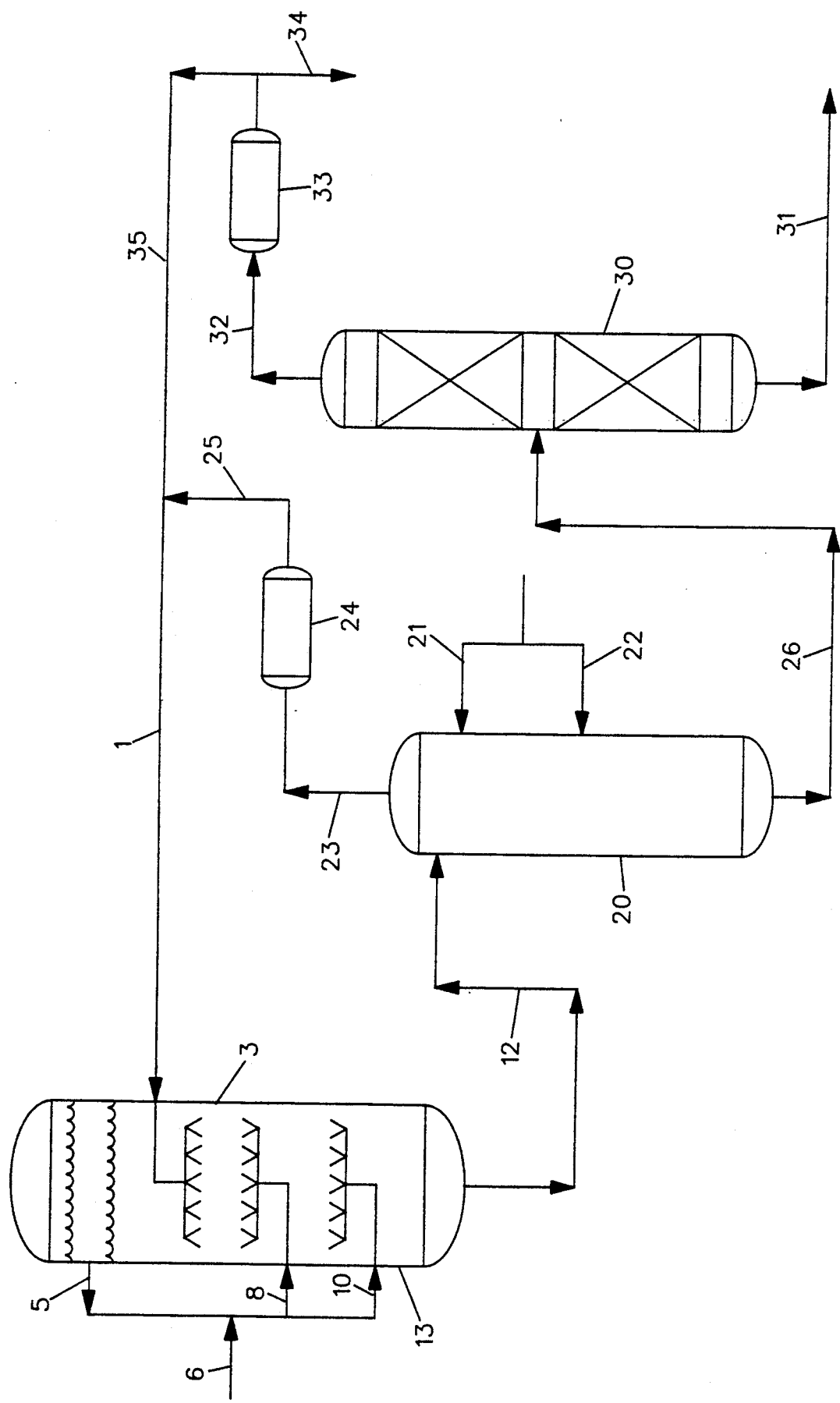
FIG. 2 is a schematic diagram of an integrated process for producing 4-IBAP utilizing an extractor-reactor having an optional finishing zone, an HF removal column, and a light ends column, in accordance with this invention.

Referring now to FIG. 2, the operation of extractor-reactor 3 is carried out as indicated in the description of FIG. 1 with the IBB feed stream fed to the middle or the bottom of extractor-reactor 3, and with the acetylating agent dissolved in liquid HF, entering extractor-reactor 3 through line 1, being a mixture of acetyl fluoride and, in most cases, acetic acid obtained as recycle streams from HF-removal column 20 and, possibly, light ends column 30. The composition of HF-acetylating mixture in line 1 is such that the mole ratio of HOAc:AcF ranges from about 0:1 to about 2:1, with the more preferred mole ratio of HOAc:AcF ranging from about 0.25:1 to about 2:1, and the most preferred mole ratio of HOAc:AcF ranging from about 0.65:1 to about 1.3:1. The HF content of the mixture is varied as necessary. Typically, the mole ratio of (HOAc+AcF) to HF ranges from about 1:5 to about 1:25, with a preferred mole ratio of (HOAc+AcF) to HF ranging from about 1:10 to about 1:20.

Reactor product from the bottom of extractor-reactor 3 comprising 4-IBAP, HF, AcF, and HOAc, with all or most of the 4-IBAP complexed with HF, is transported as feed to the top of HF-removal column through line 12. Acetic anhydride is injected into column 20 through two lines, line 21 slightly below the point of entry of the feed stream in line 12, and/or line 22 lower down the column, in sufficient quantity to react with substantially all the HF complexed with 4-IBAP or acetic acid, as shown in parent application Ser. No. 07/445,055, filed Dec. 4, 1989. The products of this reaction are AcF and additional HOAc. Free and liberated HF, AcF and HOAc, as well as a portion of unreacted IBB, are withdrawn from column 20 as an overhead stream through line 23, and, after passing through condenser 24, are recycled to extractor-reactor 3 through lines 25 and 1. In the alternative, the column can be operated such that the overload stream through line 23 comprises only HF and AcF, with all of the HOAc being withdrawn as part of a bottom stream comprising 4-IBAP and HOAc. Such bottom stream is withdrawn through line 26 and flows to light ends column 30, where it is separated into a bottom stream composed largely of 4-IBAP which is withdrawn through line 31, and an overhead stream composed largely of HOAc withdrawn through line 32. The 4-IBAP-containing bottom stream 31 may be sent to a heavy ends column (not shown) for the removal of impurities less volatile than 4-IBAP and the 4-IBAP may also be subjected to other purification treatments before being further utilized. The overhead HOAc-containing stream 32 from column 30 is condensed in condenser 33 and can be recycled as stream 35 to extractor-reactor 3 in combination with condensed overhead stream 25 from HF-removal column 20, as the feed through line 1 previously described. Any remainder of the HOAc-containing stream from light ends column 30 is withdrawn from the system through line 34.

The following examples further illustrate the invention.

EXAMPLE 1

An extractor-reactor 3 constructed from 20 ft. of 8" pipe was packed in two section with ⅝" pall rings as shown in FIG. 1. The reactor was maintained at 58° C. and at a pressure sufficient to prevent the solvents from boiling, i.e., about 40 to 60 psig. To the top of the reactor through line 1 were fed 185 lb/hr of an HF solution containing 19 wt.% AcF and 15.2 wt.% HOAc, obtained, as shown in FIG. 2, as recycle streams from HF-removal column 20 and light ends column 30, and which form a continuous, dense HF-rich phase. As shown in FIG. 1, an IBB feed stream was fed through line 10 at a rate of 74 lb/hr to the bottom of the reactor, with flow to the middle of the reactor being blocked. A discontinuous light IBB-rich phase formed at the bottom of the reactor, which being less dense and largely insoluble in the continuous HF-rich phase, percolated to the top of the vessel. Reaction occurred between the AcF and possibly some of the HOAc as acetylating agent, and the IBB to form 4-IBAP, which was extracted into the continuous HF-rich phase, and HF and possibly water, respectively, as by-product. IBB-rich phase containing unreacted IBB collected at the top of the vessel and after phase separation, was recycled through line 5 and eventually line 10 as part of the IBB feed (which comprises both recycle IBB and makeup IBB) to the bottom of the vessel in an amount of 58.8 lb/hr. Fresh IBB in an amount of 15.2 lb/hr was continuously added through lines 6 and 10 to replace that used up in the reaction and dissolved in the HF-rich phase. From the bottom of extractor-reactor 3, 200 lb/hr of the HF-rich phase was removed containing, in addition to the HF in the feed stream and that formed as by-product in the acetylation reaction, the desired product, 4-IBAP, along with unreacted IBB, AcF, HOAc and other by-products. A sample of the exiting HF-rich stream withdrawn at P4 was treated to remove HF by quenching in ice water, neutralizing, and extracting with an organic solvent. After stripping away the solvent, the organic fraction remaining was found to contain 55.1 wt.% of 4-IBAP and 37.5 wt.% of IBB. Analysis of a sample of IBB feed stream withdrawn at P3 indicated the presence of 0.3 wt.% of 4-IBAP, 57.6 wt.% of IBB, and 1.8 wt.% of fluoride derived from HF and AcF.

The HF-rich product stream from extractor-reactor 3 was fed through line 12 to HF-removal column 20 containing 30 trays where Ac$_2$O was introduced to react with HF complexed with 4-IBAP and HOAc and form AcF, and light components primarily HF and AcF, were stripped overhead for recycle to extractor-reactor 3 through line 1, as referred to the first part of this example and described in parent application Ser. No. 07/445,055. The HF-rich feed stream was fed near the top of column 30 at trays 26, 28 or 30. The Ac$_2$O in an amount of 14 lb/hr was fed to column 20 below the feed point of the HF-rich feed stream, with a major proportion of Ac$_2$O being fed at trays 20 or 24 and a minor proportion at trays 6, 9 or 14. A product stream in an amount 49 lb/hr was removed from the base of column 20 through line 26 and contained 26.9 wt.% of 4-IBAP, 5.9 wt.% of IBB, 61.6 wt.% of HOAc, 2.1 wt.% of Ac$_2$O, and other by-products.

The product stream from HF removal column 20 was further purified by feeding it through line 26 to light ends distillation column 30 where the bulk of the HOAc was separated as an overhead stream from the 4-IBAP product at a pressure of 10–50 mm Hg pressure. The overhead stream, suitable for recycle to extractor-reactor 3, was withdrawn through line 32 and condensed in line 33; it contained 88.1 wt.% of HOAc, 3.5 wt.% of Ac$_2$O and 5.9 wt.% of IBB. The product stream in an amount of about 14.4 lb/hr was removed through line 31 and contained 91.6 wt.% of 4-IBAP, with the bulk of the remainder being higher boiling by-products. The latter were substantially removed by further purification in a heavy ends distillation column.

EXAMPLE 2

The configuration of equipment was the same as in Example 1, but IBB was fed to the middle of the extractor-reactor instead of the bottom, so that the bottom part of the vessel acted as a "finishing zone" wherein additional residence time for the continuous HF-rich phase provided for further reaction between the acetylating agent, mostly AcF, and dissolved IBB in a homogeneous system, thus increasing the yield of 4-IBAP. The temperature of the reactor was maintained at 60° C. To the top of the reactor through line 1 were fed 290 lb/hr of HF containing 6.8 wt.% AcF and 10.3 wt.% HOAc. IBB was fed through line 8 at a rate of 89 lb/hr to the middle of the reactor. 16.4 lb/hr of IBB were continuously added through line 6 to replace that used up in the reaction and dissolved in the HF-rich phase, and 307 lb/hr HF solution were removed from the bottom of the reactor through line 12. Analysis of the organic fraction of this stream as in Example 1 indicated 78.7 wt.% of 4-IBAP and 13.3 wt.% of IBB, and analysis of a sample obtained from the middle of extractor-reactor 3 at P2 indicated 66.4 wt.% of 4-IBAP and 27.7 wt.% of IBB.

The stream exiting from extractor-reactor 3 through line 12 was fed separately with 13 lb/hr of Ac$_2$O to the thirty tray HF removal stripping column 20 as in Example 1. A solution was continuously withdrawn from the bottom of the column having a composition of 34.0 wt.% 4-IBAP, 0.3 wt.% of IBB, 59.9 wt.% of HOAc, 3.0 wt.% of Ac$_2$O and other by-products.

Separation of HOAc from the crude acetylation product of HF removal column 20 was accomplished by distillation in light ends column 30 at 10–50 mm Hg pressure as in Example 1. The overhead stream from the distillation contained 94.8 wt.% of HOAc, 4.6 wt.% of Ac$_2$O, and 0.5 wt.% of IBB. A product stream composed of 92.2 wt.% of 4-IBAP was continuously removed from the base of the column.

EXAMPLES 3 TO 24

The procedure and equipment used to operate extractor-reactor 3 in these samples were similar to those of Examples 1 and 2 except that certain conditions such as feed stream rates and temperature were varied. Table I shows the rates of product withdrawn through line 12 ("Product Rate"), the IBB feed rate through lines 8 or 10 ("IBB Feed"), the HF and acetylating agent feed rate through line 1 ("HF Feed"), the IBB makeup rate through line 6 ("IBB Makeup"), the mode of operation ("Mode") with "1" indicating that IBB was fed to the middle of extractor-reactor 3 through line 8 as in Example 2, and "2" indicating that IBB was fed to the bottom of extractor-reactor 3 through line 10 as in Example 1, and the temperature of operation ("Temp").

TABLE I

| Example | Product Rate lb/hr | IBB* Feed lb/hr | HF Feed lb/hr | IBB Makeup lb/hr | Mode | Temp. °C. |
|---|---|---|---|---|---|---|
| 3 | 112 | 100 | 103 | 9.2 | 1 | 59.3 |
| 4 | 214 | 256 | 204 | 10.4 | 1 | 58.6 |
| 5 | 145 | 128 | 133 | 12.0 | 1 | 60.2 |
| 6 | 133 | 262 | 117 | 16.1 | 2 | 58.3 |
| 7 | 135 | 239 | 118 | 17.3 | 2 | 61.1 |
| 8 | 195 | 133 | 176 | 18.4 | 1 | 60.0 |
| 9 | 198 | 185 | 187 | 11.2 | 1 | 59.1 |
| 10 | 197 | 106 | 184 | 12.8 | 1 | 73.7 |
| 11 | 115 | 50 | 112 | 2.3 | 1 | 69.2 |
| 12 | 201 | 52 | 177 | 24.3 | 1 | 73.0 |
| 13 | 205 | 104 | 182 | 23.0 | 2 | 74.4 |
| 14 | 126 | 48 | 114 | 12.3 | 2 | 73.2 |
| 15 | 180 | 95 | 169 | 10.9 | 1 | 60.8 |
| 16 | 306 | 91 | 295 | 11.0 | 1 | 54.4 |
| 17 | 313 | 92 | 302 | 10.7 | 1 | 53.7 |
| 18 | 301 | 87 | 286 | 15.1 | 1 | 55.6 |
| 19 | 299 | 85 | 287 | 11.3 | 1 | 56.8 |
| 20 | 300 | 93 | 268 | 31.9 | 2 | 63.3 |
| 21 | 335 | 13 | 318 | 16.3 | 1 | 58.7 |
| 22 | 342 | 20 | 329 | 13.1 | 1 | 55.2 |
| 23 | 263 | 116 | 247 | 15.3 | 1 | 60.5 |
| 24 | 319 | 115 | 299 | 20.5 | 1 | 60.8 |

*Includes recycle IBB and makeup IBB

The compositions of various streams as indicated by the analyses of samples withdrawn at points P1, P2, P3 and P4 shown in FIG. 1, are given in Table IL

TABLE II

| Example | HF Feed, P1 [AcF] wt. % | HF Feed, P1 [HoAc] wt. % | Reactor Middle, P2 Organic Fraction [4-IBAP] wt. % | Reactor Middle, P2 Organic Fraction [IBB] wt. % | Reactor Bottom, P4 Organic Fraction [4-IBAP] wt. % | Reactor Bottom, P4 Organic Fraction [IBB] wt. % | IBB Feed, P3 [4-IBAP] wt. % | IBB Feed, P3 [IBB] wt. % | [F] wt. % |
|---|---|---|---|---|---|---|---|---|---|
| 3 | 8.5 | 9.7 | 70.6 | 19.0 | 77.6 | 7.2 | | | |
| 4 | 4.8 | 9.8 | 71.7 | 22.3 | 83.1 | 9.9 | | | |
| 5 | 4.8 | 3.8 | 69.3 | 16.2 | 70.2 | 7.1 | | | |
| 6 | 11.6 | 4.3 | | | 64.5 | 18.6 | | | |
| 7 | 15.2 | 4.3 | | | 67.0 | 19.8 | | | |
| 8 | 15.7 | 5.1 | 68.1 | 22.9 | 76.1 | 8.2 | | | |
| 9 | 8.8 | 10.7 | 70.2 | 22.8 | 79.9 | 13.0 | | | |
| 10* | 14.4 | 3.8 | 63.3 | 21.2 | 83.7 | 2.0 | | | |
| 11 | 19.4 | 15.1 | 50.7 | 38.2 | 59.2 | 25.9 | | | |
| 12 | 15.1 | 5.7 | 60.8 | 15.5 | 65.1 | 7.0 | | | |
| 13 | 4.7 | 5.5 | | | 63.3 | 16.3 | | | |
| 14 | 5.4 | 13.2 | | | 63.8 | 19.8 | | | |
| 15 | 11.7 | 10.3 | | | | | 0.0 | 76.5 | 2.9 |
| 16 | 9.6 | 10.2 | 63.9 | 25.6 | 81.7 | 11.5 | | | |
| 17 | 10.6 | 9.9 | | | 77.1 | 15.7 | 0.0 | 57.0 | 3.3 |
| 18 | 4.1 | 10.5 | | | 70.2 | 25.0 | 0.05 | 65.0 | 1.4 |
| 19 | 4.5 | 10.4 | | | 83.7 | 11.1 | | | |
| 20 | 15.1 | 11.2 | | | 67.0 | 26.8 | | | |
| 21 | 9.4 | 6.3 | | | | | 0.19 | 80.4 | 2.2 |
| 22 | # | 6.1 | 78.5 | 17.0 | 88.7 | 6.4 | | | |
| 23 | 6.8 | 10.1 | 49.6 | 44.1 | 81.5 | 11.8 | | | |
| 24 | 9.3 | 8.4 | 61.2 | 31.1 | 75.5 | 15.3 | | | |

*Analytical results show low accountability
Estimated to be 7 wt %

The results summarized in Table II of the examples carried out under mode 1, which provided for a finishing zone allowing for additional acetylation reaction between dissolved IBB and acetylating agent in homogenous system, indicate that the production stream leaving the bottom of the extractor-reactor always has a higher percentage of 4-IBAP than the mixture entering the finishing zone at the middle of the extractor-reactor just below the IBB feed point. This demonstrates that significant additional acetylation of dissolved IBB does indeed occur in the finishing zone. Furthermore, a comparison of the results of the mode 1 examples with those carried out under mode 2, wherein no finishing zone was utilized, indicates that the product stream leaving the bottom of the extractor-reactor when it was operated in mode 1 tended in most cases to have a higher percentage of 4-IBAP than was the case when the extractor-reactor was operated in mode 2. Thus, the utilization of a finishing zone or reactor is in most cases beneficial in providing for higher overall yields of 4-IBAP.

The scope of the invention also includes a second embodiment wherein IBB forms the continuous phase and the HF-rich phase forms the discontinuous phase, which HF-rich rich phase migrates downward through the IBB phase. The HF-rich phase collects in the bottom of the extractor-reactor for further processing in a manner similar to that described in the preferred embodiment above.

The embodiments described above are not intended to place undue limitations on the scope of the present invention, particularly regarding non-critical features of the invention, wherein one skilled in the art can make modifications and equivalent substitutions which provide obvious variations of the invention. Such variations are intended to fall within the scope of the present invention as defined in the following claims:

We claim:

1. A continuous process for the production of 4-isobutylacetophenone (4-IBAP) comprising feeding liquid hydrogen fluoride (HF) and an acetylating agent into an extractor-reactor to form a first, HF-rich phase containing said acetylating agent, feeding isobutylbenzene (IBB) to the extractor-reactor to form a second, IBB-rich phase which is contacted with said first, HF-rich phase in a manner such that the acetylating agent reacts with IBB to form 4-IBAP which is extracted into said first, HF-rich phase, and a light IBB-rich second phase containing the bulk of unreacted IBB; externally recycling said second, IBB-rich phase to said IBB feed point in combination with fresh IBB to make up for IBB consumed in the reaction and that dissolved in said HF-rich phase, and withdrawing an HF-rich stream containing 4-IBAP from the extractor-reactor.

2. The process of claim 1 wherein said acetylating agent comprises acetyl fluoride.

3. The process of claim 2 wherein said acetylating agent substantially consists of a combination of acetic acid and acetyl fluoride.

4. The process of claim 2 wherein said acetylating agent substantially consists of a combination of acetic anhydride and acetyl fluoride.

5. The process of claim 2 wherein said acetylating agent substantially consists of a combination of acetic acid, acetic anhydride and acetyl fluoride.

6. The process of claim 1 wherein said HF-rich phase is the continuous phase and said IBB-rich phase is the discontinuous phase.

7. The process of claim 1 wherein said HF-rich phase below the IBB feed point is held in a finishing zone or reactor for a time sufficient to provide for additional acetylation of IBB dissolved in said HF-rich phase.

8. The process of claim 7 wherein said acetylating agent comprises acetyl fluoride.

9. The process of claim 8 wherein said acetylating agent substantially consists of a combination of acetic acid and acetyl fluoride.

10. The process of claim 8 wherein said acetylating agent substantially consists of a combination of acetic anhydride and acetyl fluoride.

11. The process of claim 8 wherein said acetylating agent substantially consists of a combination of acetic acid, acetic anhydride and acetic fluoride.

12. The process of claim 7 wherein said HF-rich phase is the continuous phase and said IBB-rich phase is the discontinuous phase.

13. The process of claim 1 wherein the HF-rich stream containing dissolved 4-IBAP from said extractor-reactor is fed to an HF removal column together with acetic anhydride ($Ac_2O$) which is fed below the feed point of said HF-rich stream, the conditions of the HF-removal column being such that the $Ac_2O$ reacts with the HF complexed with 4-IBAP and any acetic acid (HOAc) present in said HF-rich feed stream to form acetyl fluoride (AcF) and additional HOAc, free and liberated HF, AcF, IBB, and optionally HOAc, are stripped from the mixture in the column and withdrawn as an overhead stream at least part of which is recycled as feed to said extractor-reactor, and a product stream comprising 4-IBAP and HOAc is withdrawn from the bottom of the column.

14. The process of claim 13 wherein the composition fed to said extractor-reactor has a mole ratio of HOAc:AcF of (HOAc+AcF) to HF of about 1:5 to about 1:25.

15. The process of claim 14 wherein said mole ratio of HOAc:AcF is from about 0.25:1 to about 2:1, and said mole ratio of (HOAc+AcF) to HF is from about 1:10 to about 1:20.

16. The process of claim 15 wherein said mole ratio of HOAc:AcF is from about 0.65:1 to about 1.3:1.

17. The process of claim 13 wherein the bottom stream withdrawn from said HF removal column is fed to a light ends column operated under conditions such that the acetic acid is separated and withdrawn as an overhead stream, and product stream containing a major proportion of 4-IBAP is withdrawn from the bottom of the column.

18. The process of claim 17 wherein at least part of said acetic acid in said overhead stream of said light ends column is recycled to said extractor-reactor.

19. The process of claim 8 wherein the HF-rich stream containing dissolved 4-IBAP from said extractor-reactor is fed to an HF removal column together with acetic anhydride ($Ac_2O$) which is fed below the feed point of said HF-rich stream, the conditions of the HF-removal column being such that the $Ac_2O$ reacts with the HF complexed with 4-IBAP and any acetic acid (HOAc) present in said HF-rich feed stream to form acetyl fluoride (AcF) and additional HOAc, free and liberated HF, AcF, IBB, and optionally HOAc are stripped from the mixture in the column and withdrawn as an overhead stream at least part of which is recycled as feed to said extractor-reactor, and a product stream comprising 4-IBAP and HOAc is withdrawn from the bottom of the column.

20. The process of claim 19 wherein the composition fed to said extractor-reactor has a mole ratio of HOAc:AcF of from about 0:1 to about 2:1 and a mole ratio of (HOAc+AcF) to HF of about 1:5 to about 1:25.

21. The process of claim 20 wherein said mole ratio of HOAc:AcF is from about 0.25:1 to about 2:1, and said mole ratio of (HOAc+AcF) to HF is from about 1:10 to about 1:20.

22. The process of claim 21 wherein said mole ratio of HOAc:AcF is from about 0.65:1 to about 1.3:1.

23. The process of claim 19 wherein the bottom stream withdrawn from said HF removal column is fed to a light ends column operated under conditions such that the acetic acid is separated and withdrawn as an overhead stream, and product stream containing a major proportion of 4-IBAP is withdrawn from the bottom of the column.

24. The process of claim 23 wherein at least part of said acetic acid in said overhead stream of said light ends column is recycled to said extractor-reactor.

* * * * *